United States Patent [19]

Redl et al.

[11] Patent Number: 4,631,055
[45] Date of Patent: Dec. 23, 1986

[54] APPARATUS FOR APPLYING A TISSUE ADHESIVE

[75] Inventors: Heinz Redl; Georg Habison, both of Vienna, Austria

[73] Assignee: Immuno Aktiengesellschaft fur chemisch-medizinische Produkte, Vienna, Austria

[21] Appl. No.: 705,725

[22] Filed: Feb. 26, 1985

[30] Foreign Application Priority Data

Mar. 29, 1984 [AT] Austria .................................. 1063/84

[51] Int. Cl.$^4$ ............................................. A61M 5/00
[52] U.S. Cl. ..................................... 604/82; 604/191; 222/135
[58] Field of Search ................. 604/82, 191, 272, 225; 222/135, 136

[56] References Cited

U.S. PATENT DOCUMENTS 4,040,420 8/1977 Speer ...................................... 604/82
4,359,049 11/1982 Redl et al. ............................ 128/218

OTHER PUBLICATIONS

Control of Upper Gastrointestinal Hemorrhage by Endoscopic Spraying of Clotting Factors", *Gastroenterology* by Linscheer and Fazio, 77:642–646 (1979).

*Primary Examiner*—Stephen C. Pellegrino
*Attorney, Agent, or Firm*—Burns, Doane, Swecker & Mathis

[57] ABSTRACT

There is disclosed an arrangement for applying a tissue adhesive based on human or animal proteins to seamlessly or seam-supportingly connect human or animal tissue or organ parts, to seal wounds, stop bleedings and the like. The tissue adhesive is formed in situ by combining solutions of the proteins and of blood-clot-promoting coagulation factors. The arrangement includes a plurality of containers ending in joining pieces for accommodating the components to be applied. A connecting head is attachable to the joining pieces of the containers, which includes a separate conveying channel for each of the components to be applied. In order to design an arrangement of the above defined kind to be troublefree and to render it usable even for hardly accessible application sites, without requiring an exchange of parts of the arrangement at an interruption of the component flow, and to be able to use it with and without the help of an endoscope, the connecting head includes an additional conveying channel for a medicinal gas. This channel leads to the front side of the connecting head parallel and closely adjacent the remaining conveying channels. The connecting head is continued in either a multi-lumen catheter containing a gas-conveying channel or in a mixing needle.

2 Claims, 5 Drawing Figures

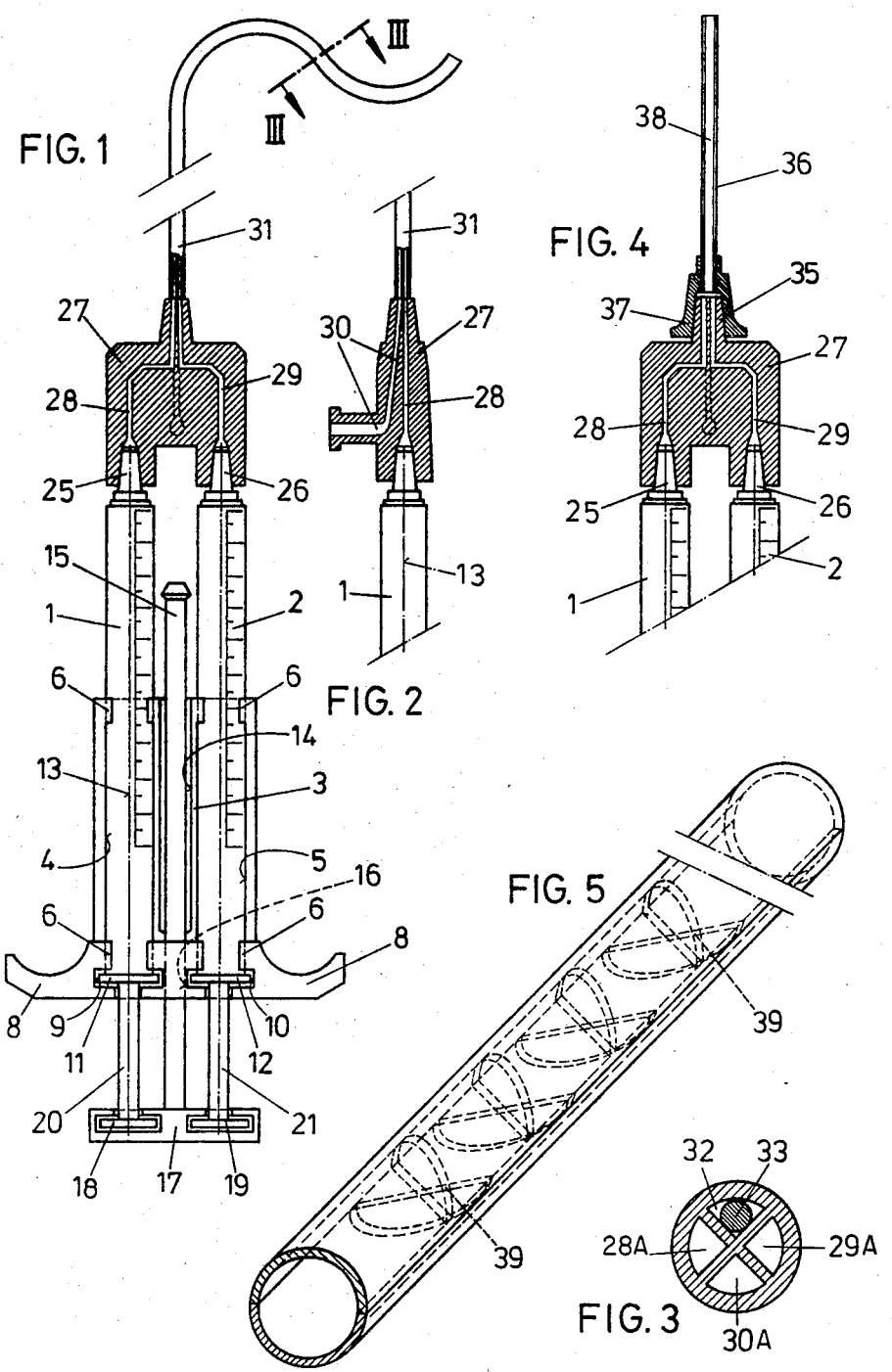

APPARATUS FOR APPLYING A TISSUE ADHESIVE

The invention relates to an arrangement for applying a tissue adhesive based on human or animal proteins to seamlessly or seam-supportingly connect human or animal tissue or organ parts, to seal wounds, stop bleedings and the like, which tissue adhesive is formed in situ by combining solutions of the proteins and of blood-clot-promoting coagulation factors, comprising a plurality of containers ending in joining pieces for accommodating the components to be applied, advantageously a plurality of standardized disposable syringe bodies of synthetic material ending in coni, a connecting head being attachable to the joining pieces of the containers, which includes a separate conveying channel for each of the components to be applied.

A known arrangement of this type is described in U.S. Pat. No. 4,359,049. As the components of the tissue adhesive, a solution containing factor XIII and fibrinogen, on the one hand, and a solution containing thrombin, on the other hand, may be used. These components are mixed in a mixing needle attached to the connecting head and are applied onto the wound area to be treated or protected.

Although the known arrangement basically has proved successful, the difficulty may arise that the tissue adhesive may set already in the mixing needle in case of an interruption of the flow of the components during application or when using long and thin mixing needles. Consequently, the mixing needle must be exchanged immediately. Such a procedure may lead to considerable disturbances in the course of a surgical operation, in particular if the site of application, e.g., in a body cavity, is not easily accessible.

A modified embodiment of the arrangement described in U.S. Pat. No. 4,359,049 comprises a spraying device for the components to be mixed, a supply channel for a sterile gas being arranged at an angle to the conveying channels of the components to be mixed. With this spraying device, a conical atomization of the components takes place at a distance of from 10 to 20 cm before the openings of the conveying channels. That arrangement, therefore, is suited for large-area applications only and also cannot be employed for hardly accessible operation regions.

Finally, an arrangement for applying coagulatable substances into body cavities has become known from a publication by Linscheer and Fazio in Gastroenterology 77, 642–646, 1979, which arrangement is comprised of a plastic catheter. The arrangement comprises a plurality of containers for the components to be mixed, to which hose conduits are connected that are inseparably connected with a multi-lumen catheter. Such an arrangement, however, has the disadvantage that there is no possibility of connecting or exchanging different application devices, that it is not preformable and that it may be employed only in connection with an endoscope, by means of which it must be guided to the site of application.

The invention aims at avoiding the disadvantages and difficulties described and has as its object to design an arrangement of the initially defined kind to be trouble-free and to render it usable even for hardly accessible application sites, wherein any interruption of the flow of the components to be mixed, which may be necessary during treatment, does not require an exchange of parts of the arrangement. Furthermore, the arrangement according to the invention is to be usable with and without the help of an endoscope.

These objects of the invention are achieved with an arrangement of the initially defined kind in that the connecting head includes an additional conveying channel for a medicinal gas, which leads to the front side of the connecting head parallel and closely adjacent the remaining conveying channels, and in that the connecting head is continued in either a multi-lumen catheter containing a gas-conveying channel or in a mixing needle.

According to an advantageous embodiment, the connecting head is made in one piece with the multi-lumen catheter or it is attachable to the connecting head in aligning connection of the conveying channels.

According to a further advantageous embodiment, the catheter, in addition to the lumina for each of the components to be applied and for the medicinal gas, includes a further lumen for a shaping wire.

Furthermore, it is possible to design the mixing needle with an internal surface that is provided with elevations and depressions promoting the turbulence of the components flowing therethrough.

With all the mentioned embodiments of the arrangement according to the invention, no obstruction can occur. By increasing the pressure of the medicinal gas, an atomization of the components may be effected at the tip of the mixing needle or at the mouth of the catheter lumen, so that the arrangement may be employed even for small-area sites of application.

The arrangement according to the invention will be explained in more detail by way of one embodiment and with reference to the accompanying drawings, wherein:

FIG. 1 is a partially sectioned side view of the arrangement according to the invention;

FIG. 2 is a partial section of the arrangement;

FIG. 3 illustrates a cross section through the catheter along line III—III of FIG. 1;

FIG. 4 illustrates a modified embodiment of the connecting head of the arrangement, including an attachable mixing needle; and FIG. 5 diagrammatically illustrates a special embodiment of a mixing needle.

By 1 and 2 two standardized disposable syringe bodies are denoted, one of which serves to accommodate a thrombin-containing solution and one of which serves to accommodate a factor-XIII and fibrinogen-containing solution. The syringe bodies 1, 2 suitably are designed as standardized disposable syringe bodies made of synthetic material. They are commonly inserted in a holding means 3. The latter comprises two U-shaped ducts 4, 5, which are each equipped with knobs 6 on their ends such that the syringe bodies 1, 2, which are inserted into the ducts from above, will snap in and are held fast by the knobs 6.

On the end of the holding means, finger grips 8 are provided, which comprise U-shaped recesses 9, 10 into which the flange ends 11, 12 of the syringe bodies project such that the syringe bodies are fixed in the direction of their longitudinal axes 13. Between the U-shaped ducts 4, 5, a gap 14 is provided for a guide rod 15 penetrating the bore 16 of the holding means in the region of the finger grips 8. The guide rod may be connected with a common actuating means 17 for the thumb yokes 18, 19 of the pistons 20, 21. These pistons, however, may be actuated also separately.

The two coni 25, 26 of the syringe bodies project into appropriately shaped recesses of the connecting head 27 and are connected therewith. Within the connecting head, a separate conveying channel 28, 29 leads from each plug-in conus 25, 26 to the front side of the connecting head. Moreover, a further conveying channel 30 is provided in the connecting head for a medicinal gas, which likewisely leads to the front side of the connecting head, parallel and closely adjacent the conveying channels 28 and 29.

The connecting head is continued in one piece (integrally) in a four-lumen catheter 31 (FIG. 3), one lumen 28A being the continuation of conveying channel 28, another lumen 29A being the continuation of conveying channel 29 and a third lumen 30A being the continuation of the air conveying channel 30, a shaping wire 33 being inserted in the fourth lumen 32. With the help of this shaping wire, the catheter may assume any desired plastic shape in order to be moved to the site of application.

By pressing the pistons 18, 19 or the actuating means 17 after previous opening of a valve (actuating the conveying channel 30, not illustrated), the components to be mixed are supplied to the site of application, while the openings of the conveying channels are reliably kept clear by continuously flowing gas.

A modified embodiment is illustrated in FIG. 4, wherein the connecting head 27, which otherwise is designed in the same manner as that of FIGS. 1 and 2, comprises a socket-like projection 35, in which the three parallel conveying channels 28, 29 and 30 are united. To this projection (which may be formed by cutting off the catheter 31 according to FIG. 1), a mixing needle 36 is attachable by means of a joining piece 37 comprising the socket 35. The interior 38 of the mixing needle may be provided with an internal surface that promotes the turbulence of the components flowing therethrough, as is illustrated in FIG. 5 on an enlarged scale, the turbulence promoting means being designed as grooves 39.

Depending on the choice of the conveying rate and on the conveying amount of the medicinal gas at the application, an emergence of the components in liquid form or an atomization of the components can be achieved at the mouth with both the embodiment comprising a catheter and the embodiment comprising a mixing needle, the arrangement thus being applicable on a large scale.

What we claim is:

1. In an apparatus for applying a tissue adhesive based on human or animal proteins to be used for seamlessly or seam-supportingly connecting human or animal tissue or organ parts, for sealing wounds, stopping bleedings and the like, said tissue adhesive being formed in situ by bringing together at least two components comprised of solutions of said proteins and blood clot-promoting coagulation factors, said apparatus comprising a plurality of disposable syringe bodies made of synthetic material and adapted to contain said components, said bodies including coni through which the components are to be expelled, a connecting head attachable to said coni, and separate component-conveying channels disposed in said connecting head for conducting said components to be applied, the improvement wherein a gas-conveying channel is provided in said connecting head for conducting a medicinal gas, said gas-conveying channel extending to a front side of said connecting head to discharge gas in a direction parallel to the discharge of said components from said component-conveying channels and closely adjacent thereto, a multi-lumen catheter formed of one-piece integral construction with said connecting head and including a plurality of component-conveying lumina communicating with respective ones of said component conveying channels, and a gas-conveying lumen communicating with said gas-conveying channel, whereby said syringes can be removed from said connecting head and integral catheter for replacement.

2. In an apparatus for applying a tissue adhesive based on human or animal proteins to be used for seamlessly or seam-supportingly connecting human or animal tissue or organ parts, for sealing wounds, stopping bleedings and the like, said tissue adhesive being formed in situ by bringing together at least two components comprised of solutions of said proteins and blood clot-promoting coagulation factors, said apparatus comprising a plurality of disposable syringe bodies made of synthetic material and adapted to contain said components, said bodies including coni through which the components are to be expelled, a connecting head attachable to said coni, and separate component-conveying channels disposed in said connecting head for conducting said components to be applied, the improvement wherein a gas-conveying channel is provided in said connecting head for conducting a medicinal gas, said gas-conveying channel extending to a front side of said connecting head to discharge gas in a direction parallel to the discharge of said components from said component-conveying channels and closely adjacent thereto, a multi-lumen catheter formed of one-piece integral construction with said connecting head and including a plurality of component-conveying lumina communicating with respective ones of said component-conveying channels, and a gas-conveying lumen communicating with said gas-conveying channel, whereby said syringes can be removed from said connecting head and catheter for replacement, and an additional lumen containing a shaping wire enabling said catheter to be shaped in desired configurations.

* * * * *